United States Patent [19]

Oren

[11] Patent Number: 4,683,322

[45] Date of Patent: Jul. 28, 1987

[54] PROCESS FOR THE PRODUCTION OF METHOMYL OXIME

[75] Inventor: Zohar Oren, Beer Sheva, Israel

[73] Assignee: Makhteshim Chemical Works Ltd., Beer Sheva, Israel

[21] Appl. No.: 805,424

[22] Filed: Dec. 4, 1985

[30] Foreign Application Priority Data

Dec. 5, 1984 [IL] Israel ......................................... 73749

[51] Int. Cl.$^4$ ........................................... C07C 119/18
[52] U.S. Cl. ....................................................... 558/3
[58] Field of Search ............................................ 558/3

[56] References Cited

U.S. PATENT DOCUMENTS 3,374,260  3/1968  Buchanan ............................... 558/3

Primary Examiner—Henry R. Jiles
Assistant Examiner—Robert C. Whittenbaugh
Attorney, Agent, or Firm—Browdy and Neimark

[57] ABSTRACT

There is provided a process for the production of alkyl-thiolhydroxamates in high yields and purity. The reaction is effected by contacting a hydroxylamine salt and an S-alkyl thiolimidic ester salt in a suitable solvent in the presence of an ammonium, alkali or alkaline earth metal carbonate or bicarbonate at a low pH and at a temperature in the 25°–50° C. range until the reaction is complete, and recovering the desired product.

8 Claims, No Drawings

PROCESS FOR THE PRODUCTION OF METHOMYL OXIME

FIELD OF THE INVENTION

The products are useful in organic synthesis, especially in the production of certain insecticides.

There is provided a process for the production of alkyl thiolhydroxamates and derivatives thereof, and especially for the production of methomyl oxime, which is also known as methyl thiolhydroxamate or methyl thiolacet-hydroxamate. The process is effected under defined conditions of pH and temperature in specific solvents, resulting in a reduced reaction time, in high yields and in a high purity of the product.

SUMMARY OF THE INVENTION

There is provided a process for the production of alkyl thiolhydroxamates and of derivatives of these, which are useful in organic synthesis and especially in the production of certain insecticides. A highly valuable product of this kind of methamyl oxime. The above products are obtained in a high yield and purity, and at a high concentration by reacting S-alkyl thiolimidic ester salts with a hydroxylamine salt in a suitable solvent in the presence of ammonium carbonate or bicarbonate, of an alkali metal carbonate or bicarbonate or an alkaline earth carbonate or bicarbonate. The reaction takes place essentially according to the following reaction scheme:

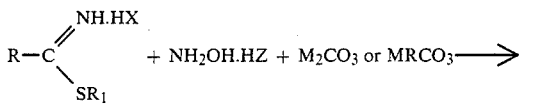

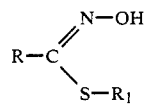

wherein R is lower alkyl, preferably $C_1$–$C_3$ alkyl or lower methoxyalkyl, $R_1$ is lower alkyl and preferably $C_1$–$C_3$ alkyl or cyano-lower alkyl, HX is an inorganic acid or inorganic acid equivalent, HZ is an inorganic acid such as hydrogen chloride or sulfuric acid, M is an alkali metal or alkaline earth metal or ammonium. The reaction is effected by mixing the reactants at a low pH, preferably below pH 0, and adding the carbonate or bicarbonate so that the pH at the end of the reaction will not exceed pH 2 to prevent base-initiated decomposition. The reaction temperature is in the range of 25° to 50° C., although this range is not critical. The preferred range is 35°–45° C.

BACKGROUND OF THE INVENTION

Methomyl oxime is a commercial product; is useful in the production of certain commercial insecticides of the carbamate and methyomyl type.

There are numerous references in the literature to the preparation of this economically useful intermediate and related alkyl thiolhyroxamates. There can be mentioned Israel Pat. No. 26,830, U.S. Pat. Nos. 3,658,869, 3,752,841 and 3,787,470. Most of these prior art references are characterized by either low yields or high reaction dilutions, where the low yields are due to the highly reactive nature of the reaction environment.

To overcome this critical environmental factor, many of the prior art synthesis have been carried out at great dilution and using a specific solvent. Thus, U.S. Pat. No. 3,987,096 discloses an aqueous process which gives yields of about 99% of methomyl oxime; but at a reaction concentration of less than 1%. Such a low concentration is particularly wasteful of energy in the steps required for economic recovery of the valuable intermediate or its ultimate products.

The yields of a similar magnitude of methomyl oxime was reported in U.S. Pat. No. 3,752,841 using diemthylformamide (DMF) as a reaction solvent. While this solvent permits reaction concentrations of 20–25%, DMF is a recognized irritant and toxicant substance requiring stringent precautions in the workplace under current safety legislation.

Recently U.S. Pat. No. 4,327,033 disclosed the preparation of methomyl oxime in good yield using N-methylpyrolidone. However, this also limits the reaction to one specific expensive, high boiling solvent which is difficult to remove.

U.S. Pat. No. 3,374,260 discloses the preparation of methomyl oxime by reacting S-alkyl thiolimidic ester salts with a hydroxylamine salt in the presence of metal alkoxides using a lower alkyl alcohol as solvent. However, this reaction requires six or more hours for completion, is limited only to specific types of alcohols, requires the use of the expensive and difficult to handle metal alkoxides, and affords low yields. Indeed, in attempting to reproduce the results of this patent the product was obtained in very low yields due to its decomposition under the basic reaction conditions. In addition, this reaction was found to have the tendency to get easily out of control and even to cause a slight explosion.

DESCRIPTION OF THE INVENTION

The present invention is based on the surprising discovery that alkylthiolhydroxamates methomyl oxime can be prepared in good yields and at high concentration by reacting S-alkyl thiolimidic ester salts with a hydroxylamine salt in the presence of ammonium or metal carbonates or bicarbonates in a variety of solvents according to the following equation:

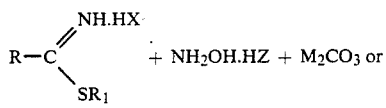

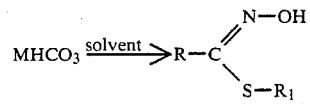

wherein R is a lower alkyl ($C_1$–$C_3$) or lower methoxyalkyl; $R_1$ is a lower alkyl ($C_1$–$C_3$) or cyanoalkyl; HX is any inorganic acid; HZ is an inorganic acid such as hydrogen chloride or sulfuric acid; M is an alkali or alkaline metal or the ammonium ion; comprising mixing the reactants initially at a pH of 0 (or less) and adding the metal carbonate or bicarbonate until the pH, at the end of the reaction, is in the region of 0–2, to prevent base-initiated decomposition while keeping the reaction at a temperature of 25°–50° C. This affords high yields of the methomyl oxime in high purity using a fairly short reaction time in a variety of solvents. Preferred S-alkyl thiolimidic ester salts are those in which R is a $C_1$-$C_3$ alkyl group; and the most preferred S-alkyl thiolimidic ester salt is that in which both R and $R_1$ are methyl.

HX may be an inorganic acid such as hydrogen chloride, hydrogen bromide or hydrogen sulfate, hydrogen chloride being preferred. HZ may be hydrogen chloride or sulfuric acid. M can be an alkali or alkaline metal ion, or the ammonium ion giving the required pH; sodium, potassium or calcium being preferred for economic reasons. The reaction proceeds with either an ammonium or alkali or alkaline metal carbonate or bicarbonate; however, the alkali or alkaline earth carbonate is preferred as it affords a higher yield.

The solvent can be the corresponding nitrile such a acetonitrile or isobutyronitrile; a hydrocarbon such as tolune, hexane, xylene, etc., or a chlorinated hydrocarbon such as dichloroethane, trichloroethane, tetrachloroethane, or carbon tetrachloride. The preferred solvents are the corresponding nitrile, toluene or dichloroethane.

In order to prevent the product from decomposing under basic reaction conditions not only is a mild base such as carbonate or bicarbonate used but the reaction is run with strict attention to the reacting pH, ending the reaction at a pH not greater than 2. To this end, the pH of the reaction must be constantly monitored and adjusted.

The reaction is ordinarily effected between 25° and 50° C., although some deviation from this range will not result in inoperability. However, for most efficient operation, it is preffered to maintain a temperature during reaction of between 35° and 40° C.

The S-alkyl thiolimidic ester salts starting materials suitable for use in the process of the present invention can be prepared by reacting the corresponding nitrile, the corresponding alkyl mercaptan, and an inorganic acid such as hydrogen chloride or hydrogen bromide in one of the solvents of the process of the invention, similar to that disclosed in Schmidt, Berichte Deutsch Chem. Ges., 47 24547(1914). The use of the same solvent has the advantage that the intermediate S-alkyl thiolimidic ester salt can be used in situ, avoiding its isolation and workup.

DESCRIPTION OF THE PREFERRED EMBODIMENT

EXAMPLE 1

To 362 g of agitated acetonitrile kept at a temperature of 0°–5° C. were simultaneously added 82 g of dry hydrogen chloride and 106 g methyl mercaptan over a period of 75 minutes. The reaction mixture was allowed to warm up to room temperature over a period of about ten hours.

The above solution of methyl thiolacetimidate hydrochloride is heated to 33° C. and 133 g of hydrocylamine hydrochloride is added. To this mixture 112 g sodium carbonate is added over a period of twenty minutes. Carbon dioxide is given off by the reaction mixture and this continues for some two and a half hours. During the entire reaction period the pH of the reaction is carefully monitored by an electrode so that the pH of the mixture at the end of the reaction is in the range of pH 0 and pH 2. Some 250–300 ml of water are added to this mixture, the mixture stirred well a few minutes, the resulting two phases separated, and the acetonitrile removed from the organic phase to afford methomyl oxime in a yield of 80–85% and a purity of 93%.

EXAMPLE 2

To 446 g of agitated isobutyronitrile kept at room temperature were simultaneously added 82 g of dry hydrogen chloride and 106 g of methyl mercaptan over a period of five hours. The reaction mixture was then warmed to 39° C. and kept at this temperature for about twelve hours.

The above solution of methyl thiolisopropyl acetimidate hydrochloride is heated to 39° C., and 133 g of hydroxylamine hydrochloride is added. To this mixture some 112 g sodium carbonate is added over a period of twenty minutes. Carbon dioxide is given off by the reaction mixture and continutes to do so for some two and a half hours. During the entire reaction the pH of the reaction is carefully monitored by an electrode so that the pH of the mixture at the end of the reaction is in the range of pH 0 and pH 2. Some 220–300 ml of water are added to this mixture, the mixture stirred well for a few minutes, the resulting two phases are separated, the aqueous layer extracted twice with isobutyronitrile, the organic layers combined, and the isobutyronitrile removed to affored methyl thiolisopropyl-hydroxamate, having an M.P. of 50–52° C.;=yield: 80% and a purity of 95%.

EXAMPLES 3–10

The process according to this invention was used in the preparation of compounds of the formula

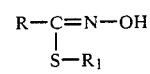

where R is lower alkyl ($C_1$–$C_3$) or lower methoxyalkyl and $R_1$ is lower alkyl ($C_1$–$C_3$) or cyanoalkyl. The process of Example 1 was repeated but using starting materials with the required functional groups to obtain the corresponding alkyl thiolhydroxamates in similar yields under similar conditions.

| Example | R | $R_1$ |
| --- | --- | --- |
| 3 | $CH_3$ | $C_2H_5$ |
| 4 | $C_3H_7$ | $CH_3$ |
| 5 | $C_3H_7$ | $C_2H_5$ |
| 6 | $C_3H_7$ | $C_3H_7$ |
| 7 | $CH_3OCH_2$ | $CH_3$ |
| 8 | $CH_3OCH_2$ | $C_2H_5$ |
| 9 | $CH_3OCH_2$ | $C_3H_7$ |
| 10 | $CH_3$ | $NCC_2H_4$ |

I claim:
1. A process for the production of alkyl thiolhydroxamates of the formula:

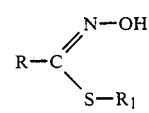

wherein
R is lower alkyl or lower methoxyalkyl;
$R_1$ is lower alkyl or cyanoalkyl, which comprises preparing a reaction mixture of:
(a) an anydrous hydroxylamine salt selected from the group consisting of hydroxylamine hydrochloride, hydroxylamine hydrobromide, hydroxylamine sulfate, and hydroxylamine acid sulfate;

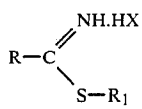

wherein R and R$_1$ are as defined; and HX is an inorganic acid selected from the group consisting of hydrogen chloride, hydrogen bromide, and hydrogne sulfate;

(c) a solvent selected from the group consisting of acetonitrile, isobutyronitrile, hydrocargon solvents, and chlorinated hydrocarbon solvents, to give a reaction mixture of pH 0; adding thereto an ammonium, alkali or alkaline earth metal carbonate or bicarbonate and maintaining the mixture at a temperature between 25° and 50° C., mixing the reactants at an initial pH of no greater than zero and maintaining the reaction until the reaction is complete while keeping the pH below 2 to the end of the reaction, and recovering the alkyl thiolhydroxamate which is formed.

2. A process according to claim 1 wherein the alkali metal carbonate is sodium carbonate, potassium carbonate or ammonium carbonate.

3. A process according to claim 1 wherein the alkali metal bicarbonate is sodium bicarbonate.

4. A process according to claim 1, wherein the hydrocarbon solvent is toluene, acetonitrile, isobutyronitrile, or dichloroethane.

5. A process according to claim 1, wherein the hydroxylamine salt is hydroxylamine hydrochloride or hydroxylamine sulfate.

6. A process according to claim 1, wherein the reaction temperature is maintained between 35° and 40° C.

7. A process in accordance with claim 1, wherein the alkali metal carbonate is sodium carbonate, the solvent is acetonitrile, the hydroxylamine salt is hydroxylamine hydrochloride, and the temperature is maintained between 35° and 40° C.

8. The process according to claim 1, wherein the S-alkyl thiolimidic ester salt is methyl thiolacethydroxamate.

* * * * *